United States Patent
Tai (10) Patent No.: US 9,591,989 B2
(45) Date of Patent: Mar. 14, 2017

(54) INSERT DEVICE FOR ENHANCING PET AND MRI IMAGES

(75) Inventor: Yuan-Chuan Tai, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 13/450,009

(22) Filed: Apr. 18, 2012

(65) Prior Publication Data

US 2012/0271149 A1 Oct. 25, 2012

Related U.S. Application Data (60) Provisional application No. 61/478,293, filed on Apr. 22, 2011.

(51) Int. Cl.

| | |
|---|---|
| *A61B 5/05* | (2006.01) |
| *A61B 5/055* | (2006.01) |
| *A61B 5/00* | (2006.01) |
| *G01R 33/48* | (2006.01) |
| *A61B 6/04* | (2006.01) |
| *A61B 6/00* | (2006.01) |
| *A61B 6/03* | (2006.01) |
| *G01R 33/34* | (2006.01) |
| *G01R 33/341* | (2006.01) |

(52) U.S. Cl.
CPC ............ *A61B 5/055* (2013.01); *A61B 5/0035* (2013.01); *A61B 6/037* (2013.01); *A61B 6/0435* (2013.01); *A61B 6/4258* (2013.01); *A61B 6/4266* (2013.01); *A61B 6/50* (2013.01); *A61B 6/501* (2013.01); *A61B 6/502* (2013.01); *A61B 6/508* (2013.01); *A61B 6/5235* (2013.01); *G01R 33/481* (2013.01); *A61B 6/4417* (2013.01); *A61B 2576/00* (2013.01); *G01R 33/341* (2013.01); *G01R 33/34053* (2013.01)

(58) Field of Classification Search
CPC ... G01R 33/481; A61B 6/4417; A61B 6/5235; A61B 6/4241; A61B 6/4258; A61B 6/4266; G01T 1/1603; G01T 1/1642
USPC .......................................................... 600/411
See application file for complete search history.

(56) References Cited

U.S. PATENT DOCUMENTS

| | | | |
|---|---|---|---|
| 6,946,658 B2 | 9/2005 | Tai | |
| 7,485,866 B2 | 2/2009 | Tai | |
| 7,835,782 B2 | 11/2010 | Cherry et al. | |
| 2003/0090267 A1* | 5/2003 | Rubashov | 324/318 |
| 2006/0124855 A1* | 6/2006 | Gagnon | A61B 6/037 250/370.09 |
| 2008/0077005 A1* | 3/2008 | Piron et al. | 600/411 |

(Continued)

OTHER PUBLICATIONS

Woody et al., Preliminary studies of a simultaneous PET/MRI scanner based on the RatCAP small animal tomograph, Nuclear Instruments and Methods in Physics Research A 571 (2007) 102-105.*

(Continued)

*Primary Examiner* — Long V Le
*Assistant Examiner* — Ellsworth Weatherby
(74) *Attorney, Agent, or Firm* — Armstrong Teasdale LLP (57) ABSTRACT

Insert devices that include a RF surface coil and gamma-ray photon detector array for enhancing PET and MRI images produced from integrated PET-MRI scanners are disclosed. Integrated PET-MRI scanners that include such insert devices as well of methods for scanning an object by use of such devices are also disclosed.

15 Claims, 5 Drawing Sheets

(56) References Cited

U.S. PATENT DOCUMENTS

| | | | |
|---|---|---|---|
| 2008/0088309 A1* | 4/2008 | Eberler et al. | 324/318 |
| 2009/0195249 A1* | 8/2009 | DeMeester et al. | 324/318 |
| 2009/0299170 A1* | 12/2009 | Gebhardt | A61B 5/055 600/411 |
| 2010/0106004 A1* | 4/2010 | Harvey | 600/411 |
| 2011/0084211 A1* | 4/2011 | Yamaya et al. | 250/363.03 |
| 2012/0136237 A1* | 5/2012 | Benlloch Baviera et al. | 600/411 |

OTHER PUBLICATIONS

Pichler et al., Latest Advances in Molecular Imaging Instrumentation, The Journal of Nuclear Medicine, vol. 49, No. 6 (Suppl), Jun. 2008.*

Janecek et al., "A Simulation Study for the Design of Prototype Insert for Whole-Body PET Scanners", 2006, IEEE Transactions on Nuclear Science, 2006, pp. 1143-1149, vol. 53, No. 3.

Judenhofer et al., "Simultaneous PET-MRI: a new approach for functional and morphological imaging", Nature Medicine, 2008, pp. 459-465, vol. 14, No. 4.

Pal et al., "2D linear and iterative reconstruction algorithms for a PET-insert scanner", 2007, Phys. Med. Biol., pp. 4293-4310, vol. 52.

Schlemmer et al., "Simultaneous MR/PET Imaging of the Human Brain", Radiology, 2008, vol. 248, No. 3.

Tai et al., "Initial Study of an Asymmetric PET System Dedicated to Breast Cancer Imaging", IEEE Transactions on Nuclear Science, 2006, pp. 121-126, vol. 53, No. 1.

Tai et al., "Virtual-Pinhole PET", The Journal of Nuclear Medicine, 2008, pp. 471-479, vol. 49, No. 3.

Wu et al., "Micro Insert: A Prototype Full-Ring PET Device for Improving the Image Resolution of a Small-Animal Pet Scanner", Journal of Nuclear Medicine, 2008, pp. 1668-1676, vol. 49, No. 10.

Schwaiger et al., "MR-PET: Combining Function, Anatomy, and More", Special Molecular Imaging, 2005, pp. 25-30.

* cited by examiner

INSERT DEVICE FOR ENHANCING PET AND MRI IMAGES

CROSS-REFERENCE TO RELATED APPLICATION

This application claims the benefit of U.S. Provisional Application No. 61/478,293, filed Apr. 22, 2011, which is incorporated herein by reference.

STATEMENT REGARDING FEDERALLY SPONSORED RESEARCH & DEVELOPMENT

This disclosure was made with government support under grants CA110011 and CA083060, awarded by the National Institutes of Health. The government has certain rights in the invention.

BACKGROUND

Dual modality scanners are being developed to provide anatomical and functional information at the same time. PET-MRI integrated scanners have been developed such as, for example, the scanner disclosed in U.S. Pat. No. 7,835,782 which is incorporated herein be reference for all relevant and consistent purposes. PET-MRI integrated scanners allow for the strengths of both modalities to be combined thereby providing improved images.

A continuing need exists for methods for locally enhancing the resolution and sensitivity of MRI and PET images and, in particular, for enhancing images produced from PET-MRI integrated scanners. A continuing need also exists for devices that reliably achieve such image enhancement and for devices that can be removably coupled to an existing PET-MRI integrated scanner.

SUMMARY

One aspect of the present disclosure is directed to an insert device for enhancing PET and MRI images produced from an integrated PET-MRI imaging scanner. The insert device includes a device housing, an RF surface coil for detecting radio-frequency signals, and a gamma-ray photon detector array for detecting positrons. The RF surface coil and gamma-ray photon detector array are located within the housing.

Another aspect of the present disclosure is directed to an integrated PET-MRI imaging scanner for imaging an object. The scanner includes a main RF coil for generating radio-frequency signals, a first gamma-ray photon detector array for detecting positrons, a RF surface coil for detecting radio-frequency signals, and a second gamma-ray photon detector array for detecting positrons.

Yet a further aspect of the present disclosure is directed to a method for imagining an object by use of an integrated PET-MRI imaging scanner. The integrated PET-MRI scanner includes a main RF coil for generating radio-frequency signals and a first gamma-ray photon detector array for detecting positrons. The method includes positioning an insert device for enhancing PET and MRI images in the scanner. The insert device includes a device housing, an RF surface coil for detecting radio-frequency signals and a second gamma-ray photon detector array for detecting positrons. The RF surface coil and gamma-ray photon detector array are located within the housing.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

Corresponding reference characters indicate corresponding parts throughout the drawings.

DETAILED DESCRIPTION

In accordance with the present disclosure, an insert device for enhancing both PET and MRI images produced from an integrated PET-MRI imaging scanner is provided. The insert device includes both an RF surface coil for locally detecting radio-frequency signals and a gamma-ray photon detector array (synonymously a "gamma-ray detector array") for detecting positrons and locally enhancing the PET signal. Generally the RF surface coil and gamma-ray photon detector array are incorporated into a housing for reversibly positioning the insert device into an existing integrated PET-MRI imaging scanner to locally enhance images produced therewith.

Positron Emission Tomography ("PET") is an imaging technique that provides three-dimensional tomographic images of a distribution of positron-emitting isotopes within an object. The object is usually a living human or animal, and the images provide a visual depiction of functional differences within different portions of the object. A PET procedure involves the introduction of radiolabeled tracing pharmaceuticals into the object, usually through injection or inhalation. The type of pharmaceuticals depends on the function of the tissue under investigation. As the radiolabeled tracing element in the pharmaceutical decays, it produces positrons. Each positron collides with surrounding matter in the sample object before combining with an electron in the sample object. The combination of each positron with an electron in the sample object annihilates both particles, producing a pair of gamma-ray photons. The gamma-ray photons travel away from the annihilation event in opposite directions. If a pair of opposing gamma-ray detectors each detect one of the two gamma-ray photons produced in the annihilation event within a predetermined period of time, usually 3 to 20 nanoseconds, a "coincidence event" is recorded, and it is assumed the annihilation event producing the gamma-ray photons lies along a straight line between the two detectors.

Conventionally, a PET scanner includes arrays of gamma-ray detectors, arranged either continuously as one or multiple rings, or as two or more detector plates. Lines of response ("LOR") are formed between opposing detector pairs in each array. The PET scanner obtains the radioactivity distribution information within the object by detecting annihilation events originating along each LOR. Commercially available PET scanners having one or more rings of detectors are available for PET scanning animal and human subjects. The inside diameters of the rings of detectors for PET scanning animal and human subjects are approximately 15 centimeters and 80 centimeters, respectively. Conventionally, for scanners having detectors arranged in rings, the object is placed at the center of the rings where the sampling is believed to be the highest, hence achieving the best resolution and image quality currently available. For scanners having detector plates, the detector plates rotate around the object to collect data from all angles in order to form a complete set of projections of the distribution. For the same reason as the ring configuration, the object is conventionally centered between the detector plates. The detection of a large number of annihilation events allows a computer to construct a three-dimensional image of the distribution of radiolabeled pharmaceuticals within the object, providing valuable information on the kinetics of the pharmaceuticals and functions of the living object.

With these conventional designs, the image spatial resolution of a PET system is determined by several factors, including intrinsic detector spatial resolution, acolinearity of the annihilating gamma-ray photons, and positron range of the radioisotopes in the tracing pharmaceuticals. Of these three factors, the positron range depends on the type of radioisotopes used and does not depend on the scanner design; the effect of acolinearity depends on the ring diameter or distance between detector plates of a PET scanner, which are often pre-determined by the necessary imaging field of view in order to accommodate the body of a human or an animal. Therefore, PET scanner manufacturers have been trying to improve scanner spatial resolution by designing new detectors that improve the detector's intrinsic spatial resolution. This is particularly important for very high resolution PET scanners dedicated to small animal imaging, which are very powerful tools for the advancement of molecular imaging.

For most animal PET scanners and some state-of-the-art human scanners, discrete scintillation crystals coupled to photodetectors have been used to achieve the highest spatial resolution heretofore possible. For a PET scanner using discrete crystals, the detector intrinsic spatial resolution cannot be better than one half of the crystal width. For a PET scanner with ring geometry, the detector pairs form sampling lines with an average sampling distance of half a crystal width. Based on the Nyquist theorem in sampling theory, the smallest object (i.e., the highest frequency of signal) one system can resolve is twice the size of the sampling distance (i.e., half of the sampling frequency). In order to achieve image spatial resolution approaching the theoretical limit, where the detector intrinsic spatial resolution equals one half the crystal width, conventional PET scanners require smaller sampling distances. Many attempts have been made to increase the sampling resolution. For example, certain designs move the detector or the object by a fraction of the detector width. Other designs stack discrete crystals in multiple offset layers. With these designs, image resolution can begin to approach the detector intrinsic resolution. However, conventional PET scanners have been unable to achieve image resolution higher than the detector intrinsic spatial resolution regardless of the type of gamma-ray detector employed. This is true for PET scanners with scintillation detectors, ionization chambers, semiconductor detectors and other types of gamma-ray detectors.

Magnetic resonance imaging (MRI) is an alternative imaging technique that uses a coil (i.e., a radio frequency transmitter) to produce an electromagnetic field. The magnetic field causes the magnetic moment of some of the protons to change and align with the direction of the field. As the field is turned off, the photons decay to their original state with the difference in energy between the two states being discharged as a electromagnetic radiation. This released radiation is detected by a coil to thereby construct an image of the scanned object. Similar to PET, MR imaging may be plagued by poor special resolution.

In this regard, the insert device of the present disclosure is typically incorporated into an existing integrated PET-MRI imaging scanner such as the scanner disclosed in U.S. Pat. No. 7,835,782 or the scanner described by Schlemmer et al. in "Simultaneous MR/PET Imaging of the Human Brain: Feasibility Study," *Radiology*, vol. 248:3 (2008), both of which are incorporated herein for all relevant and consistent purposes. Generally, the scanner will include an RF coil for generating an electric field. In normal use (i.e., use without application of the insert device of the present disclosure), photons produced upon termination of the magnetic field may be detected by this main detector or may be detected on a second RF coil within the scanner. The scanner will also include one or more gamma-ray photon detector arrays (e.g., opposing first and second gamma-ray photon detector arrays) for detecting positrons emitted from the object. Each array is composed of a series of detectors such as, scintillation crystals, ionization chambers, semiconductor materials or any other material for detecting gamma-ray photons. The arrays may be arranged according to any of the arrangements shown in U.S. Pat. No. 7,485,866 which is incorporated herein by reference for all relevant and consistent purposes. Prior to scanning, radiolabeled tracing pharmaceuticals are introduced into the object to be imaged. As the radioisotopes in the tracing pharmaceuticals decay, they produce positrons. Each positron collides with surrounding matter in the object and eventually combines with an electron and annihilates, producing a pair of gamma-ray photons. The gamma-ray photons travel away from each other in a straight line. When the gamma-ray photons strike the detectors, they are detected.

The existing integrated PET-MRI imaging scanner in which the insert device of the present disclosure is used may be sized and shaped for whole-body scanning of a human subject or may be sized and shaped for animal imaging (e.g., large or small animal MRI). Further, the PET-MRI imaging scanner may be sized and shaped for scanning a certain organ such as for example, a human brain, a heart, a prostate or the like.

In this regard, the integrated PET-MRI scanners described above are exemplary and scanners other than as described may be used without departing from the scope of the present disclosure.

The insert device of the present disclosure generally includes a gamma-ray photon detector array for locally enhancing images produced by detecting positrons. The array is composed of a series of detectors such as, scintillation crystals, ionization chambers, semiconductor materials or any other material for detecting gamma-ray photons. The detectors within the array may be of the same type and the same size. Alternatively, the detectors may be of the same type but different sizes, or of different types altogether.

Preferably, the array has intrinsic spatial resolution equal to or better than the intrinsic spatial resolutions of the existing integrated PET-MRI scanner in which the insert coil is used. Better intrinsic spatial resolution, in other words resolution capable of distinguishing smaller structures of the object, may be achieved through a variety of known methods including, for example, decreasing the size of detectors.

It should be noted that in embodiments wherein the integrated MRI-PET scanner contains two gamma-ray photon detector arrays for normal PET imaging (i.e., imagining without use of the insert device of the present disclosure), when the insert device is used, one of the arrays may generally be inoperable as its operation is replaced by the array of the insert device. In some other embodiments, both arrays used during normal imaging may also be used with the array of the insert device (e.g., the scanner may include electronics and/or processing dedicated to the insert coil itself which becomes operable after insertion of the insert device).

The insert device of the present disclosure also includes a RF surface coil for locally enhancing MR images produced after application of an electromagnetic field by the main RF coil of the integrated PET-MRI scanner. A number of different surface coil geometries may be used such single-looped or multiple-looped surface coils which may have a circular or rectangular geometry.

Figure 1:
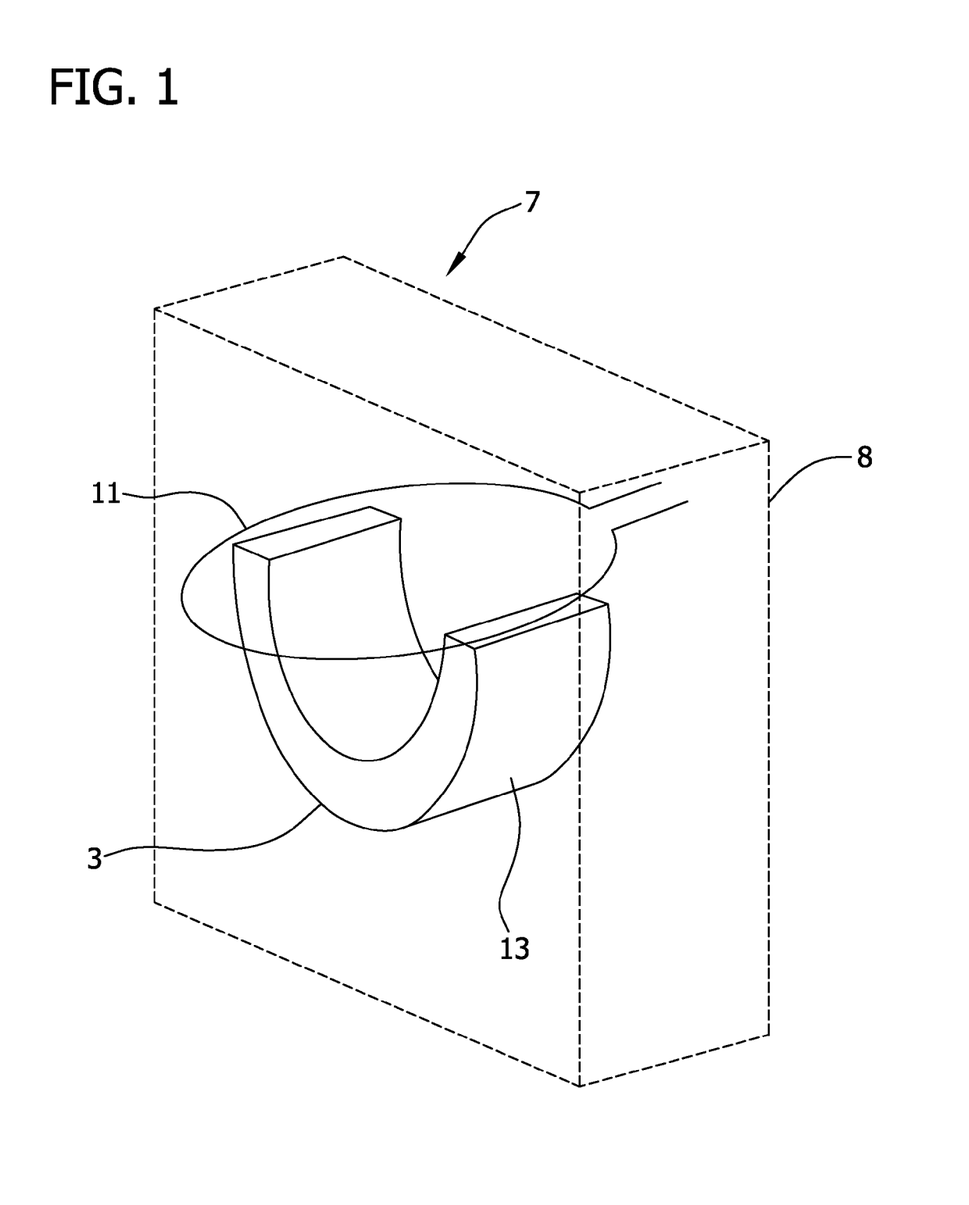
FIG. 1 is an isometric view of an insert device according to one embodiment of the present disclosure with the housing thereof being shown in transparent for clarity.

Referring now to FIG. 1, an exemplary insert device 7 for use in an integrated MRI-PET scanner is shown. The device 7 includes a housing 8 which is shown as being transparent in FIG. 1 for clarity. The housing 8 may be made of any material suitable for imaging applications such as, for example, low density foam and carbon fibers. The device 7 includes a gamma-ray photon detector array 13 and an RF surface coil 11 within the housing 8. It should be noted that the device 7 may include more than one surface coils 11 or more than one gamma-ray photon detector arrays 13 therein without limitation.

Figure 4:
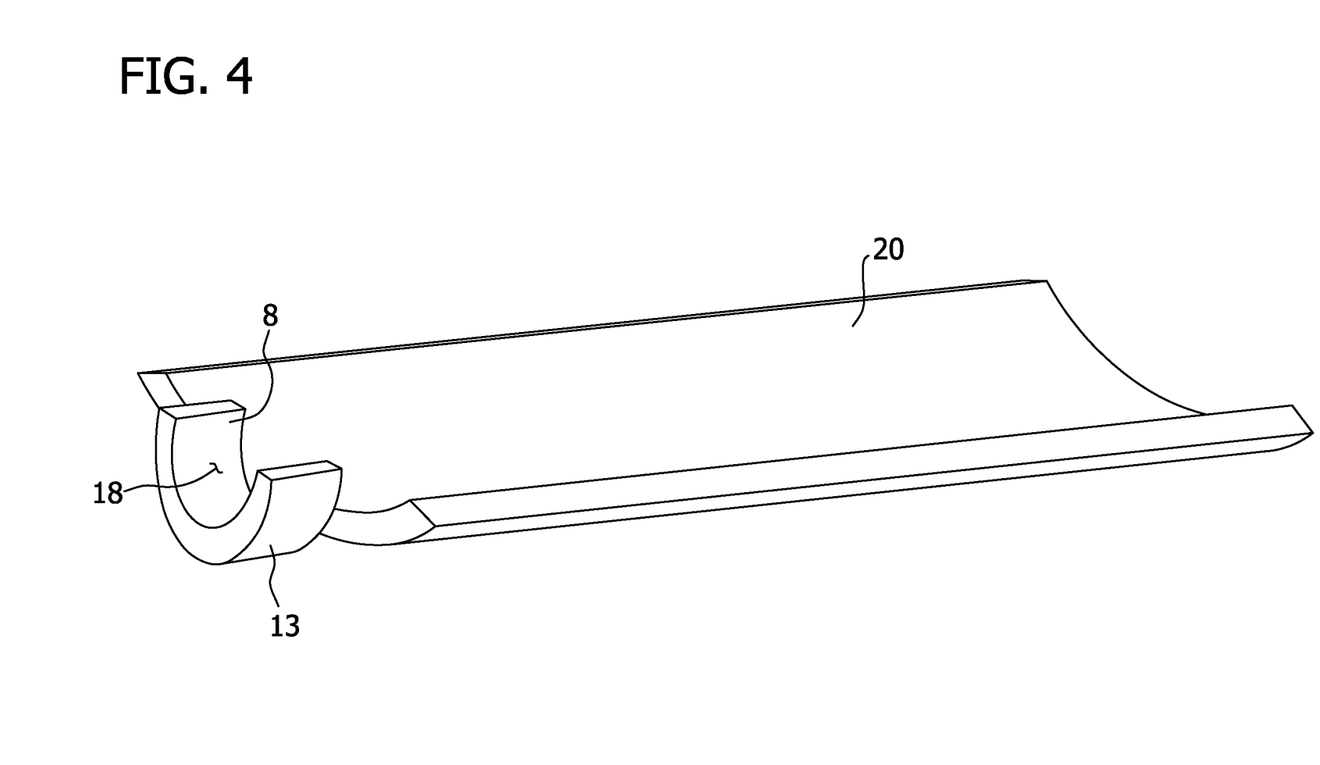
FIG. 4 is an isometric view of the insert device, the insert device being semicircular and being mounted in a different configuration relative to the stage.

The gamma-ray photon detector array 13 includes a number of detectors (not shown) therein for detecting positrons. The detectors are spaced within the semi-circular housing 3 of FIG. 1. It should be noted that in some embodiments of the present disclosure, the housing 3 of FIG. 1 may take shapes other than a semi-circle. For instance, the housing 3 may be planar or polygonal or even tubular. It should also be noted that in some embodiments of the present disclosure, the RF surface coil 11 may be located within this semi-circular housing 3 and the device 7 does not include a separate device housing 8 (FIG. 4). It should also be noted that the housing 8 may take shapes other than a box. For instance, the housing 8 may be semicircular (e.g., for imaging of the brain or the breast) or may be annular or semispherical (e.g., the imaging object is placed at the center of the annulus or semi-sphere). The housing 8 may be somewhat planar for imaging of the brain or prostate (or as in some embodiments, for placement within a blood vessel as in embodiments wherein the device is relatively miniaturized). Alternatively or in addition, the housing 8 may have one or more openings (now shown) through which an object may be placed (e.g., a human breast) for imaging.

Figure 2:
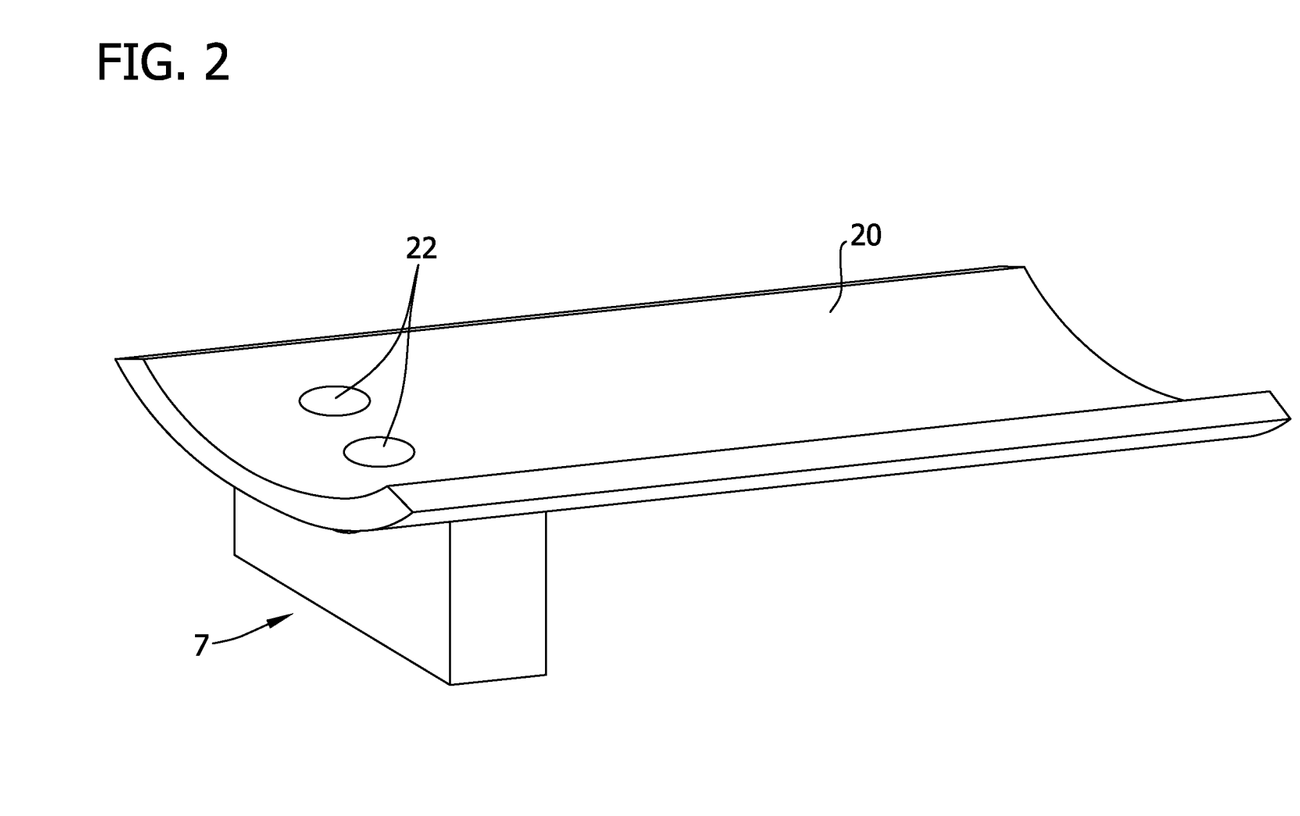
FIG. 2 is an isometric view of the insert device mounted below a stage for supporting a patient to be imagined.
Figure 3:
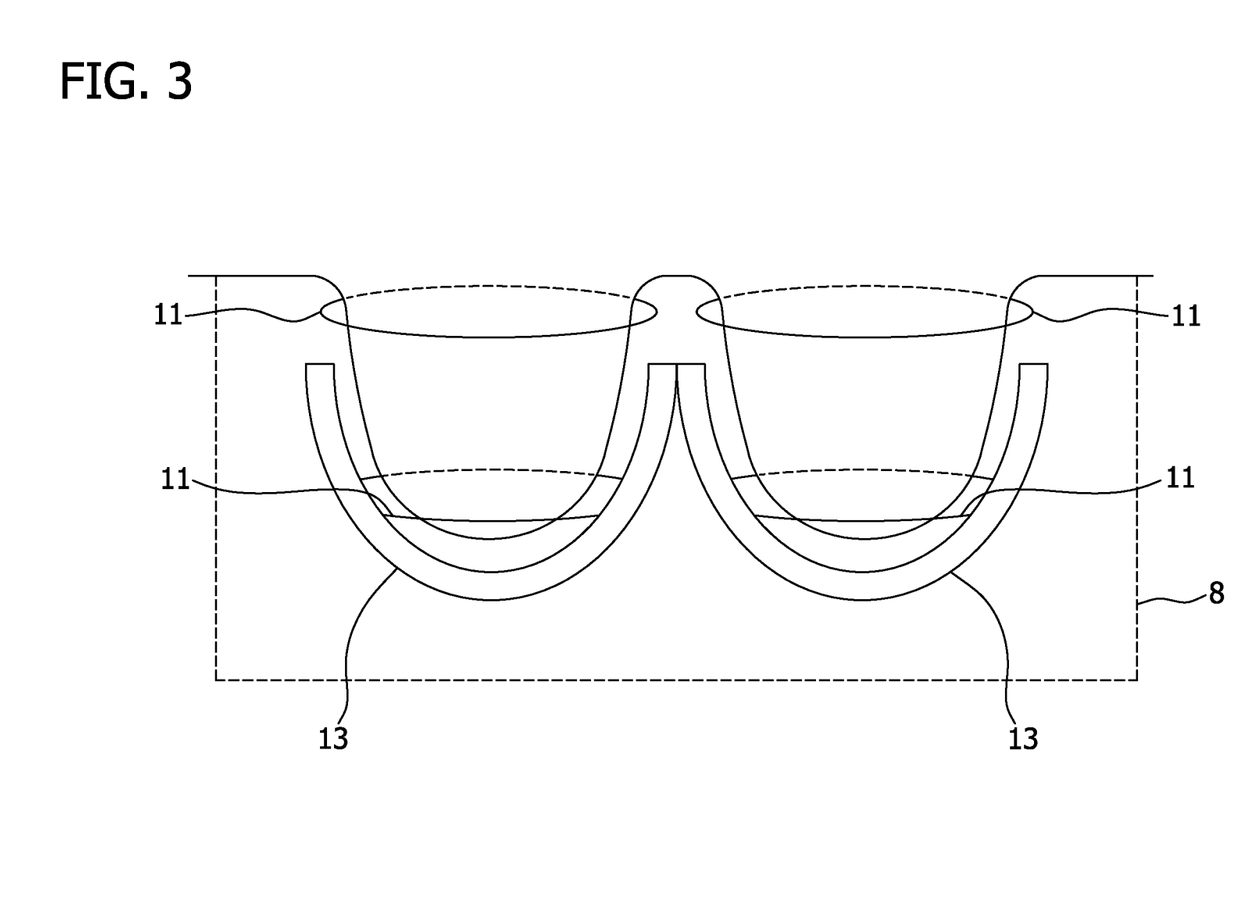
FIG. 3 is schematic view of the insert device in use for imagining of the human breast.

Referring now to FIG. 2, the insert device 7 may be located below a stage 20 which supports the body during imaging. The stage 20 may include one or more openings 22 through which a breast may be positioned for imaging of the breast. In some embodiments, the scanner may be used in conjunction with an upper body support device which may be placed on the upper surface of a stage or bed. The patient lies in the prone position and, in embodiments wherein breast imagining is desired and with reference to FIG. 3, the breasts fall within two openings and the insert device 7 of the present disclosure may be used for imaging.

In an alternative arrangement and as shown in FIG. 4, the device 7 may be positioned at the end of the stage 20. The device 7 shown in FIG. 4 has a semicircular housing 8 with a RF surface coil and gamma-ray photon detector array therein (not shown). This semicircular arrangement allows the head of a patient to be placed within the inward space 18 formed by the housing 8 for imaging of the brain.

In this regard, the device 7 may form part of a system for enhancing PET and MRI images. In addition to the device, the system may further include a mounting unit (not shown) for positioning the gamma-ray photon detector array and RF surface coil into the integrated PET-MRI imagining scanner. The specific design of the mounting unit will depend on the configuration of the integrated PET-MRI imagining scanner and/or the size and/or shape of the insert device 7 and may be determined readily by those of skill in the art. The system for enhancing PET and MRI images may also include a processing unit (e.g., a unit that forms part of the scanner itself) for producing images of the object. Electronic signals generated upon detection of RF signals by the RF surface coil and upon detecting positrons on the first and second gamma-ray photon detector are transmitted to the processor to produce an image. Alternatively, the insert device may include a processor associated with it (typically separate from the housing) and the electronic signals may be transmitted to this additional processor to produce images.

Figure 5:
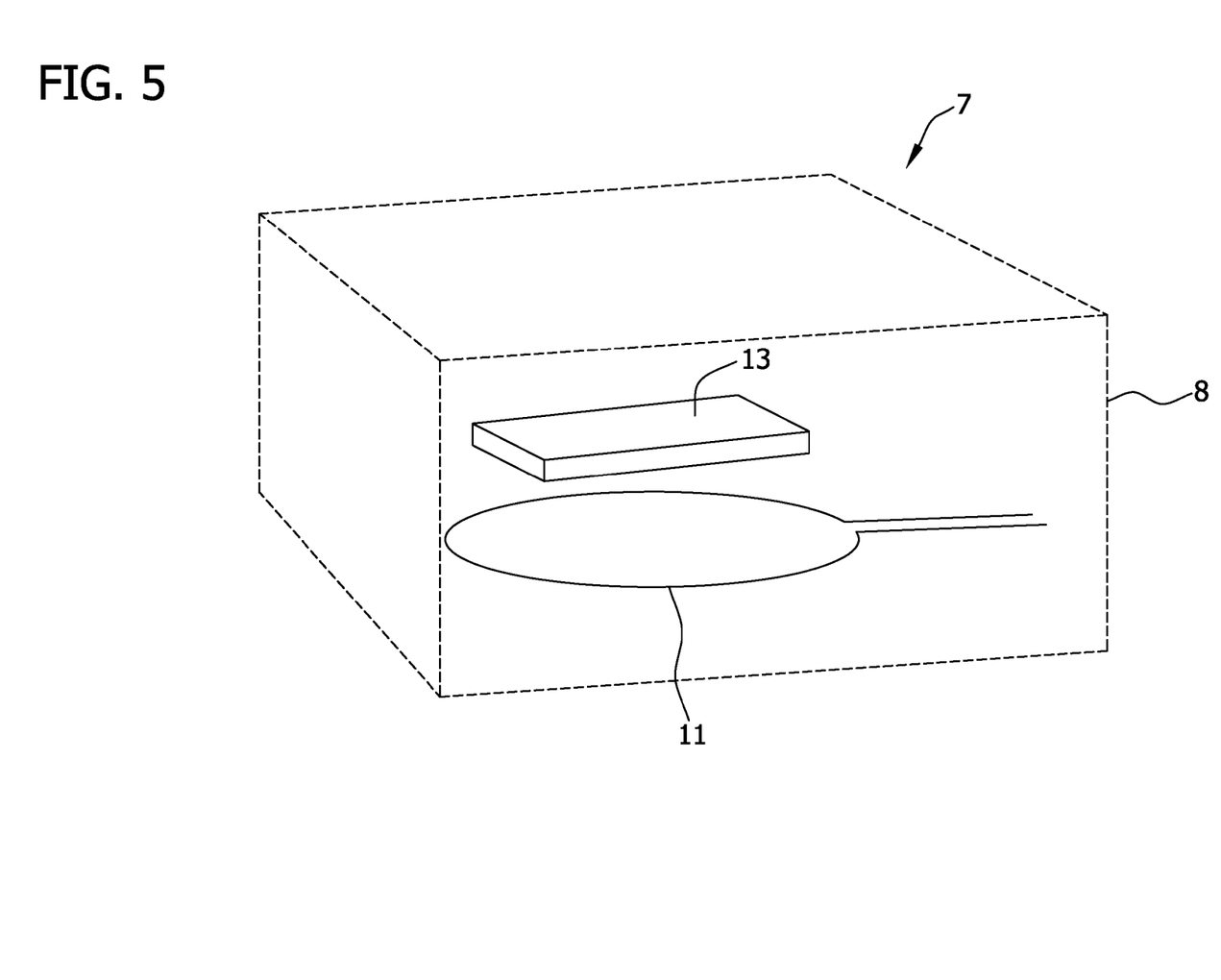
FIG. 5 is an isometric view of the insert device according to a second embodiment of the present disclosure with the housing thereof being shown in transparent for clarity.

In some embodiments and as shown in FIG. 5, the gamma-ray photon detector array 13 and/or housing 8 may be planar (e.g., similar to shape to a cell phone) and may be relatively smaller than the device of FIG. 1. This more compact planer configuration allows the device 7 to be used to image objects such as the brain, heart, colon or prostate or a specific tumor.

In this regard, the RF surface coil 11 and gamma-ray photon detector array 13 should be used in a manner that minimizes interference between the coil and array. This may be done by manipulating the geometry between the coil 11 and array 13 and by enclosing the gamma photon detectors and their electronics in a metal enclosure (also known as Faraday cage) to minimize the crosstalk between the coil 11 and array 13 caused by electromagnetic radiation. In this regard, methods for correlating the RF surface coil 11 and photon detector array 13 and for minimizing or eliminating interference is within the skill of those of ordinary skill in the art.

It should be noted that in embodiments wherein the integrated MRI-PET scanner contains two gamma-ray photon detector arrays for normal PET imaging (i.e., imagining without use of the insert device of the present disclosure), when the insert device is used, one of the arrays may generally be inoperable as its operation is replaced by the array of the insert coil. In some other embodiments, both of the gamma-ray photon detector arrays used during normal operation are also used after insertion and operation of the insert device.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the disclosure, it is intended that all matter contained in the above description and shown in the accompanying figures shall be interpreted as illustrative and not in a limiting sense.

What is claimed is:

1. An insert device for enhancing PET and MRI images of an object produced from an integrated PET-MRI imaging scanner, the insert device comprising:
   a device housing positionable within the integrated PET and MRI imaging scanner;
   an insert RF surface coil for detecting radio-frequency signals, the insert RF surface coil being located within the device housing and configured to detect RF signals generated after application of an electromagnetic field by a main RF coil of the integrated PET-MRI imaging scanner to improve an MRI imaging resolution of the integrated PET-MRI imaging scanner; and
   an insert gamma-ray photon detector array for detecting gamma-ray photons, the insert gamma-ray photon detector array being located within the device housing and configured to detect a gamma-ray photon from a positron annihilation event opposite to a corresponding gamma-ray photon from the same positron annihilation event detected with a main gamma-ray photon detector included in the integrated PET-MRI imaging scanner, wherein the detected gamma-ray photon and the corresponding detected gamma-ray photon are used to construct a line of response with enhanced accuracy to improve a PET imaging resolution of the integrated PET-MRI imaging scanner; and
   a mounting unit configured to position the insert gamma-ray photon detector array closer to the object than the main gamma-ray photon detector and further configured to position the insert RF surface coil closer to the object than the main RF coil within the integrated PET-MRI imaging scanner.

2. The insert device as set forth in claim 1, the insert device being annular or semi-spherical.

3. The insert device as set forth in claim 1, the insert device being semi-circular.

4. The insert device as set forth in claim 1, the insert device being planar.

5. An integrated PET-MRI imaging scanner for imaging an object, the integrated PET-MRI imaging scanner comprising:
   a main RF coil for generating radio-frequency signals;
   a main gamma-ray photon detector array for detecting gamma-ray photons; and
   an insert device for selectively positioning an insert RF surface coil and an insert gamma-ray photon detector array in the integrated PET-MRI imaging scanner, wherein the insert comprises:
      a device housing;
      the insert RF surface coil for detecting radio-frequency signals, the insert RF surface coil being located within the device housing and configured to detect RF signals generated after application of an electromagnetic field by the main RF coil to improve an MRI imaging resolution of the integrated PET-MRI imaging scanner;
      the insert gamma-ray photon detector array for detecting gamma-ray photons, the insert gamma-ray photon detector array being located within the device housing and configured to detect a gamma-ray photon from a positron annihilation event opposite to a corresponding gamma-ray photon from the same positron annihilation event detected with the main gamma-ray photon detector, wherein the detected gamma-ray photon and the corresponding detected gamma-ray photon are used to construct a line of response with enhanced accuracy to improve a PET imaging resolution of the integrated PET-MRI imaging scanner; and
      a mounting unit configured to position the insert gamma-ray photon detector array closer to the object than the main gamma-ray photon detector and further configured to position the insert RF surface coil closer to the object than the main RF coil within the integrated PET-MRI imaging scanner.

6. The integrated PET-MRI imaging scanner as set forth in claim 5, the scanner further comprising a second main gamma-ray photon detector array for detecting gamma-ray photons, wherein the mounting unit is further configured to position the insert gamma-ray photon array closer to the object than the second main gamma-ray photon detector array during scanning.

7. A method for imaging an object by use of an integrated PET-MRI imaging scanner, the integrated PET-MRI imaging scanner comprising a main RF coil for generating radio-frequency signals and a main gamma-ray photon detector array for detecting gamma-ray photons, the method comprising:
   positioning an insert device for enhancing PET and MRI images in the integrated PET-MRI imaging scanner, the insert device comprising:
      a device housing;
      an insert RF surface coil for detecting radio-frequency signals, the insert RF surface coil being located within the device housing and configured to detect RF signals generated after application of an electromagnetic field by the main RF coil to improve an MRI imaging resolution of the integrated PET-MRI imaging scanner, wherein the insert RF surface coil is positioned closer to the object than the main RF coil; and
      an insert gamma-ray photon detector array for detecting gamma-ray photons, the insert gamma-ray photon detector array being located within the device housing and configured to detect a gamma-ray photon from a positron annihilation event opposite to a corresponding gamma-ray photon from the same positron annihilation event detected with the main gamma-ray photon detector, wherein the detected gamma-ray photon and the corresponding detected gamma-ray photon are used to construct a line of response with enhanced accuracy to improve a PET imaging resolution of the integrated PET-MRI imaging scanner, wherein the insert gamma-ray photon detector array is positioned closer to the object than the main gamma-ray photon detector;
   positioning an object to be imaged within the integrated PET-MRI imaging scanner; and
   scanning the object.

8. The method as set forth in claim 7 wherein the object is scanned by:
   generating RF signals from the main RF coil;
   detecting RF signals on the insert RF surface coil;
   detecting gamma-ray photons on the main gamma-ray photon detector array; and
   detecting gamma-ray photons on the insert gamma-ray photon detector array.

9. The method as set forth in claim 7 wherein the scanner further comprises a second main gamma-ray photon detector array for detecting gamma-ray photons, and the method further includes positioning the insert gamma-ray photon detector array closer to the object than the second main gamma-ray photon detector array.

10. The method as set forth in claim 9 wherein the second main gamma-ray photon detector array is inoperable during scanning.

11. The method as set forth in claim 9 wherein the second main gamma-ray photon detector array is operable during scanning.

12. The method as set forth in claim 7 wherein the integrated PET-MRI imaging scanner comprises a processing unit for producing images of the object, based upon electronic signals generated upon detection of RF signals by the insert RF surface coil and upon detecting gamma-ray photons on the main and insert gamma-ray photon detector arrays being transmitted to the processor.

13. The method as set forth in claim 7 wherein the insert device comprises a processor configured to receive electronic signals generated upon detection of RF signals by the insert RF surface coil and upon detecting gamma-ray photons on the main and insert gamma-ray photon detector arrays.

14. The method as set forth in claim 7 comprising incorporating a radioactive tracer into the object prior to scanning.

15. The method as set forth in claim 7 wherein the scanner is configured for scanning a whole human body.

\* \* \* \* \*

UNITED STATES PATENT AND TRADEMARK OFFICE
CERTIFICATE OF CORRECTION

PATENT NO. : 9,591,989 B2
APPLICATION NO. : 13/450009
DATED : March 14, 2017
INVENTOR(S) : Yuan-Chuan Tai

Page 1 of 1

It is certified that error appears in the above-identified patent and that said Letters Patent is hereby corrected as shown below:

In the Specification

Column 1, Lines 14-17, delete "This disclosure was made with government support under grants CA110011 and CA083060, awarded by the National Institutes of Health. The government has certain rights in the invention." and insert therefor -- This invention was made with government support under CA110011 and CA083060 awarded by the National Institutes of Health. The government has certain rights in the invention. --.

Signed and Sealed this
Sixteenth Day of July, 2019

Andrei Iancu
*Director of the United States Patent and Trademark Office*